United States Patent [19]

Erickson

[11] 4,377,579

[45] Mar. 22, 1983

[54] N-(TETRAZOL-5-YL)PHENAZINE-1-CARBOXAMIDES

[75] Inventor: Edward H. Erickson, Woodbury, Minn.

[73] Assignee: Minnesota Mining and Manufacturing Company, St. Paul, Minn.

[21] Appl. No.: 326,853

[22] Filed: Dec. 3, 1981

[51] Int. Cl.$^3$ ............... A61K 31/495; C07D 241/46
[52] U.S. Cl. ................................. 424/250; 544/347
[58] Field of Search ...................... 544/347; 424/250

[56] References Cited

U.S. PATENT DOCUMENTS

| | | | |
|---|---|---|---|
| 3,455,926 | 7/1969 | Fouche et al. | 544/347 |
| 3,642,997 | 2/1972 | Shen et al. | 544/347 |
| 3,678,051 | 7/1972 | Leimgruber et al. | 544/347 |
| 3,887,574 | 6/1975 | Ellis et al. | 424/269 |
| 3,905,989 | 9/1975 | Hodson et al. | 424/269 |
| 4,112,094 | 9/1978 | Sellstedt et al. | 424/250 |
| 4,147,694 | 4/1979 | Erickson | 546/169 |
| 4,232,024 | 11/1980 | Winter et al. | 424/251 |

FOREIGN PATENT DOCUMENTS

| | | | |
|---|---|---|---|
| 1462194 | 7/1967 | France | 544/347 |
| 1068985 | 5/1967 | United Kingdom | 544/347 |
| 1433774 | 4/1976 | United Kingdom . | |

OTHER PUBLICATIONS

*Chem. Abs., 81,* 96448y (1974) corresponding to German Offenlegungsschrift, No. 2,356,421.
*Chem. Abs., 82,* 16843f (1975) corresponding to German Offenlegungsschrift, No. 2,415,767.
*Chem. Abs., 84,* 180256d (1976) corresponding to German Offenlegungsschrift, No. 2,536,913.
*Chemical Communications,* pp. 1423–1425 (1970).
J. Chem. Soc. Perkin I, pp. 622–626 (1972).
"Immunology", 16, 749 (1969).

*Primary Examiner*—Donald G. Daus
*Assistant Examiner*—James H. Turnipseed
*Attorney, Agent, or Firm*—Cruzan Alexander; Donald M. Sell; Robert W. Sprague

[57] ABSTRACT

Amides obtained by reaction of aminotetrazole and certain optionally substituted phenazinecarboxylic acids are potent anti-allergic agents.

13 Claims, No Drawings

N-(TETRAZOL-5-YL)PHENAZINE-1-CARBOXAMIDES

TECHNICAL FIELD

This invention relates to physiologically active compounds which are amides obtained by condensing aminotetrazole with certain optionally substituted aromatic carboxylic acids. The invention also relates to anti-allergic compositions containing such compounds and to an anti-allergic method which involves administering compounds of the invention to mammalian organisms.

BACKGROUND ART

Various known anti-allergic agents have been derived from aminotetrazole and aromatic ring systems, such as those shown in U.S. Pat. Nos. 3,887,574 (wherein the aromatic ring system is based upon chromone, xanthone, or anthroquinone) 3,905,989 (wherein the aromatic ring system is based upon thioxanthone-10, 10-dioxides), 4,112,094 (wherein the aromatic ring system is based upon pyrazine), and 4,147,694 (wherein the aromatic ring system is based upon quinoline), German Offenlegungsschrift Nos. 2,407,744 and 2,415,767 (wherein the aromatic ring system is based upon 4-hydroxy quinoline), and 2,536,913 (wherein the aromatic ring system is based upon cinnoline), and German Pat. No. 2,356,421 (wherein the aromatic ring system is based upon benzopyrazole). It is not possible to predict in advance whether or not other aromatic ring systems will provide anti-allergic activity when aminotetrazolyl groups are bonded thereto, and the discovery of new anti-allergic agents containing aminotetrazolyl groups has required trial-and-error techniques.

DISCLOSURE OF INVENTION

The present invention provides, in one aspect, compounds of the formula

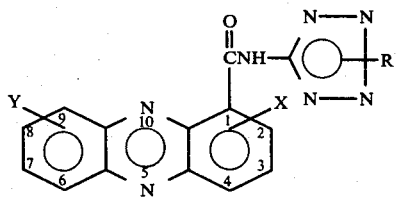

wherein R is a hydrogen atom or a lower ($C_1$–$C_4$) alkyl group, X is a hydrogen atom, halogen atom, or a methoxy or methyl group, and Y is a hydrogen atom, halogen atom, or a methoxy or ethoxy group. The present invention also provides anti-allergic compositions containing compounds of the invention together with a pharmaceutically acceptable carrier. In addition, the present invention provides a method for inhibiting allergic reactions in mammals which comprises administering compositions of the invention to such mammals.

DETAILED DESCRIPTION

In the foregoing formula, the circle in the tetrazole ring signifies a pair of double bonds which, together with the bonds shown, satisfy all of the valences of the ring carbon atom and all but one valence of the 4 ring nitrogen atoms. The remaining nitrogen valence is satisfied by R.

In the compounds of the invention in which the tetrazole ring is unsubstituted, the hydrogen atom exists in tautomeric form on either the $N^1$ or the $N^2$ atom, i.e.,

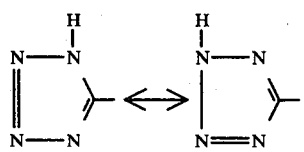

For convenience, however, hydrogen has been depicted herein simply as appearing on the $N^1$ atom. Tautomerism does not occur in compounds in which the tetrazole ring is substituted with an alkyl group, i.e., the substituent group remains in a single location.

A preferred class of compounds of the invention are those wherein R is a hydrogen atom. Another preferred class of compounds of the invention are those wherein X is a hydrogen atom. An additional preferred class of compounds of the invention are those wherein Y is a methoxy or ethoxy group. When any alkyl or alkoxy group is present in compounds of the invention, it preferably contains only one carbon atom.

The most preferred compounds of the invention have oral activity and are as follows:
N-(tetrazol-5-yl)phenazine-1carboxamide,
9-methoxy-N-(tetrazol-5-yl)phenazine-1-carboxamide,
6-ethoxy-N-(tetrazol-5-yl)phenazine-1-carboxamide,
8-ethoxy-N-(tetrazol-5-yl)phenazine-1-carboxamide, and
7-methoxy-N-(tetrazol-5-yl)phenazine-1-carboxamide,
and the preparation of these compounds is described below in Example Nos. 1, 5, 6, 7, and 8, respectively.

The compounds of the present invention preferably are prepared by reacting phenazine-1-carboxylic acids with 5-aminotetrazole or an alkyl 5-aminotetrazole. Methods for making phenazine carboxylic acids are well-known to those skilled in the art and are described, for example, in *Chemical Communications*, pp 1423–1425 (1970) and J. Chem. Soc. Perkin I, pp 622–626 (1972). Methods for making aminotetrazoles and alkyl aminotetrazoles are also well-known and are described, for example, in F. R. Benson, "The Tetrazoles", *Heterocyclic Compounds*, Vol. 8, pp 11–38 (1967).

The preferred method of preparation of the compounds of this invention employs a condensation reaction. Thus, stoichiometrically equivalent amounts of the starting materials (the phenazinecarboxylic acid and 5-aminotetrazole or alkyl 5-aminotetrazole) are dissolved or suspended in a tertiary organic amine, preferably pyridine. A stoichiometric amount of thionyl chloride is added dropwise to the above mixture. If a hydrated form of aminotetrazole starting material is used, then sufficient additional thionyl chloride is added to react with all the water of hydration. During the thionyl chloride addition, the reaction mixture is preferably maintained at a temperature of between 40° to 90° C. Other temperatures may be used, depending upon the choice of solvent, and the reflux temperature of the mixture is frequently a convenient temperature.

Alternative methods, involving reactions generally known for the synthesis of amides, may also be used to prepare the compounds of the invention. These methods involve carboxy activation, for example via acid chloride, reaction of the carboxylic acid group with N,N'-carbonyl diimidazole, reaction with N,N-dicyclohexyl carbodiimide to provide an activated adduct, reaction with ethyl chloroformate, n-butyl chloroformate and the like to provide a mixed anhydride, reaction with p-nitrophenoxybenzyl chloride to provide p-nitrophenoxybenzyl ester, and the like. These methods are generally more complex and expensive, and are only used when the preferred method is unsatisfactory.

If it is desired to prepare a (2-methyltetrazol-5-yl)phenazinecarboxamide, the synthetic route preferably involves reaction of the acid of the activated phenazinecarboxylic acid intermediate with 5-amino-2-methyl-tetrazole, or alternatively can proceed via reaction of the acid of the activated phenazinecarboxylic acid intermediate with 5-aminotetrazole followed by methylation of the tetrazole ring. Suitable methylating agents for the latter route are methyl bromide and methyl iodide. Methylation will generally result in a mixture of $N^1$ and $N^2$ substituted compounds. Separation can be carried out by crystallization or chromatography.

The compounds of the invention have been shown to inhibit the release, and/or synthesis, and/or effect of biochemical products resulting from the combination of certain types of antibody and specific antigen. Both subjective and objective changes which result from the inhibition of specific antigen by sensitized subjects may be markedly inhibited by administration of the new compounds. The new compounds are useful in the treatment of so-called "intrinsic" asthma (in which no sensitivity to extrinsic antigen can be demonstrated) or any other condition in which non-specific factors trigger the release of allergic mediators; as well as in the treatment of other conditions in which specific antigen-antibody reactions are responsible for disease, for example, smooth muscle contraction induced by spasmogens (e.g., histamine), extrinsic asthma, food allergies, allergic rhinitis, allergic conjunctivitis, atopic dermatitis, hay fever, urticaria and autoimmune diseases.

The compositions of the invention normally contain a compound of the invention (as active ingredient) in association with a pharmaceutically acceptable carrier or diluent. The nature of the composition and the carrier or diluent will depend upon the desired mode of administration, which may be, for example, orally, by inhalation (orally or nasally), parenterally (as by intradermal or intravenous injection) or by topical application. The compositions can be formulated in the conventional manner with conventional ingredients, e.g., they can be put up as solutions, suspensions, syrups, dry powders, tablets or, when intended for topical application, as creams, lotions or pastes. The compositions of the invention generally contain a minor proportion of the active ingredient and a major proportion of carrier or diluent.

For administration by inhalation, the compounds of the invention (optionally in the form of a salt such as the sodium salt) are dissolved or suspended in water and can be applied by means of a conventional nebulizer. However, the administration of medicaments by means of a pressurized dispensing container, i.e., an aerosol dispenser, is an alternative to nebulizer administration. Aqueous solutions for administration by means of a conventional nebulizer can contain up to about 10 percent by weight of the active ingredient in sterile water; and compositions for dispensing from a pressurized container containing suspensions or solutions of active ingredient in liquified propellants normally contain about 0.2 to 5 percent by weight of the active ingredient.

For administration from an aerosol dispenser, the active ingredient is dissolved or suspended in a liquified propellant medium. Suitable propellants are those conveniently used in formulations for dispensing from pressurized containers, for example, of the halogenated hydrocarbon type such as fluorohydrocarbons or fluorohalohydrocarbons and mixtures of any of these together with other propellants (see U.S. Pat. No. 2,868,691). Preferred propellants of low toxicity are difluorodichloromethane, dichlorotetrafluoroethane, and mixtures thereof. Where the active ingredient is not soluble in the propellant, it may be necessary to add a surface-active agent to the composition in order to suspend the active ingredient in the propellant medium. The use of such surface-active agents and the advantages which stem therefrom are more fully described in British Pat. No. 1,063,512.

When put up as powders, the compositions of the invention can be administered by means of a conventional insufflator device. In order to improve the properties of the powder for this purpose it is useful to modify the surface characteristics of the powder particles, for example, by coating them with a pharmaceutically acceptable material such as sodium stearate. In addition, finely divided powders containing the active ingredient can be mixed with a coarser diluent material, such as lactose, which can be present in a smaller, equal or greater amount than the amount of active ingredient, for example, in from 50 to 150 percent by weight based on the weight of the active ingredient of the invention and such other pharmaceutically active ingredients as may be present.

The compounds of the invention can also be administered by dispensers from which metered amounts of the compound are discharged to be orally or nasally received by inhalation, wherein the propellant is compressed air or any other compressed inert gas such as nitrogen, argon and the like.

As noted previously, the compounds of the invention are indicated for use in inhibiting the effects of antibody-antigen reactions. The treatment regimen may require repeated dosages of the compound at regular intervals. The amount of compound and frequency of administration will depend upon many factors, and no precise dosage rate or regimen can be stated. However, as a general guide, where the compounds are administered by inhalation to a patient suffering from acute allergic asthma, therapeutically useful results may be achieved when doses of 0.1 to 20 mg/kg are used. When the compounds are administered by oral routes, larger dosages are normally given. The invention thus provides a method for inhibiting the effects of antibody-antigen reactions by applying to the known or expected site of the antibody reaction a therapeutically effective amount of a compound of the invention.

The compounds of the invention can also be used for the treatment of allergic eye conditions, for example, those associated with hay fever, i.e., allergic conjunctivitis. For such use the compounds of the invention can be used in the form of eye drops and/or sprays as an isotonic aqueous solution containing about two percent of the compound and a preservative.

Other active ingredients can also be present in the compositions of the invention. Thus, in compositions for administration by inhalation, it can be beneficial to include a bronchodilator such as isoprenaline, adrenaline, carbuterol, rimiterol, orciprenaline, isoetharine, or derivatives thereof, particularly salts thereof. The amount of bronchodilator used will vary over a broad range, depending, inter alia, upon the nature and activity of the bronchodilator and the compound of the present invention which is used. However, the use of a minor proportion (i.e., less than 50 percent by weight) of the bronchodilator together with from 0.1 to 10 percent by weight of a compound of the invention is preferred. Such compositions constitute an additional aspect of the invention.

The effectiveness of the compounds of the invention can be evaluated by inhibiting passive cutaneous anaphylaxis in a standard test method substantially as described in "Immunology", 16, 749 (1969). The method generally used is as follows: Sprague-Dawley rates (male or female) having a body weight of about 200 grams are injected intramuscularly with egg albumin and intraperitoneally with *Bordetella Pertussis* vaccine. Ten to twelve days after this treatment the rats are exsanguinated via the abdominal aorta to recover the blood, which is allowed to clot overnight. The blood samples are centrifuged in order to remove the blood serum containing the antibody.

This antibody is used in the following way: Sprague-Dawley rats weighing from 50 to 120 grams are sensitized by intradermal injection of 0.1 ml. of antibody-containing serum into the mid-dorsal region. Sensitivity is allowed to develop for 24 hours, and the test compounds are administered (either by intraperitoneal injection or orally) at dose levels selected to provide a range of inhibition values (suitable screening doses are 50, 25, 10 or 5 mg/kg). Six rats are used for each concentration of the compound under test. At various times thereafter (e.g., five minutes), the rats are then injected intravenously with an antigen which contains 1 ml. of a mixture of egg albumin (0.5 mg/ml), Evans Blue dye solution (10 mg/ml), and physiological saline solution. Six rats are also used as controls for each test, the control rats being injected with the antibody and the antigen in the same way as the test rats but receiving no test compounds. Forty-five minutes after injection of the egg albumin the rats are killed and the skins removed and reversed. The intensity of the anaphylactic reaction is assessed by measuring the area of the characteristic blue weal produced by the spread of the Evans Blue dye from the sensitization site, with this area being determined approximately by taking the product of two diameters of the dyed area at right angles to one another. The greater the anaphylactic reaction, the larger is the area of the blue weal. Percent inhibitions are calculated using the formula $$\frac{(\text{Control Group Area} - \text{Treated Group Area}) \times 100}{\text{Control Group Area}}$$

and these values are plotted graphically for each compound so that the dosage required to achieve a 50 percent inhibition of the anaphylactic reaction ($ID_{50}$) can be determined. The compounds of the invention are active in this test at non-toxic doses, and exhibit percent inhibition of 30 percent or greater at a 5 mg. dose. The preferred compounds of Example Nos. 1, 5, 6, 7, and 8 exhibit 100, 100, 70, 83, and 88 percent inhibition, respectively, in the above test at a 5 mg. dose.

The following examples are provided for the purpose of further illustrating the invention but are not intended to limit the scope thereof in any way.

EXAMPLE 1

To a solution of 0.01 mole (2.2 g) of phenazine-1-carboxylic acid and 0.01 mole (1.0 g) of 5-aminotetrazole monohydrate in 30 ml of pyridine was added dropwise 0.02 mole (1.5 ml, 2.4 g) of thionyl chloride. While stirring, the solution began to thicken. An additional 30 ml of pyridine was added. After standing for ten minutes, the solid product was separated by filtration, washed with water, methanol and diethyl ether, and recrystallized from N,N-dimethylformamide. The product was N-(tetrazol-5-yl)phenazine-1-carboxamide, in the form of a yellow solid, m.p. 305°–306° C.(dec).

| Analysis | % C | % H | % N |
|---|---|---|---|
| Calculated for $C_{14}H_9N_7O$: | 57.7 | 3.1 | 33.7 |
| Found: | 57.7 | 3.1 | 34.0 |

EXAMPLES 2–4

Using the method of Example 1, the following compounds of the invention could be prepared from the phenazinecarboxylic acid starting materials shown below in Table I:

TABLE I

| Example no. | Phenazinecarboxylic acid starting material | Product |
|---|---|---|
| 2 | [structure: CH3O-phenazine-COOH] | [structure: CH3O-phenazine-C(=O)NH-tetrazole] |
| 3 | [structure: OCH3-phenazine-COOH] | [structure: OCH3-phenazine-C(=O)NH-tetrazole] |

TABLE I-continued

| Example no. | Phenazinecarboxylic acid starting material | Product |
|---|---|---|
| 4 | 7-ethoxyphenazine-1-carboxylic acid (CH₃CH₂O-phenazine-COOH) | 7-ethoxy-N-(1-methyl-1H-tetrazol-5-yl)phenazine-1-carboxamide |

EXAMPLE 5

To a stirred solution of 0.006 mole (1.5 g) of 9-methoxyphenazine-1-carboxylic acid and 0.006 mole (0.61 g) of 5-aminotetrazole monohydrate in 50 ml of pyridine was added dropwise 0.012 mole (1.4 g) of thionyl chloride. The mixture was warmed to 70° C., maintained at 70° C. for 20 minutes, then diluted with water. A solid product was separated from the mixture by filtration, washed with water and acetone, and dried. Recrystallization from N,N-dimethylformamide provided 9-methoxy-(N-tetrazol-5-yl)phenazine-1-carboxamide, in the form of orange needles, m.p. 325°–330° C. (dec.)

EXAMPLES 6–9

Using the method of Example 5, the following compounds of the invention were prepared from the phenazinecarboxylic acid starting materials shown below in Table II:

TABLE II

| Example no. | Phenazinecarboxylic acid starting material | Product |
|---|---|---|
| 6 | 6-ethoxyphenazine-1-carboxylic acid | m.p. 303–503° C. (dec.) |
| 7 | 8-ethoxyphenazine-1-carboxylic acid | m.p. 315° C. (dec.) |
| 8 | 8-methoxyphenazine-1-carboxylic acid | m.p. 305–307° C. (dec.) |
| 9 | 6-ethoxyphenazine-1-carboxylic acid isomer | m.p. 295–297° C. (dec.) |

EXAMPLE 10

Step A

A mixture of the known compounds 2-chloroaniline (6.3 g., 0.05 mole) and 2-bromo-3-nitrobenzoic acid (12.3 g., 0.05 mole) was refluxed overnight with 11 g. of potassium carbonate and 0.5 g. of copper-bronze in 125 ml. of ethanol. The ethanol was then removed by evaporation and the residue suspended in water. After filtration, the filtrate was acidified. A solid slowly crystallized, providing the compound 2-(2-chloroanilino)-3-nitrobenzoic acid, m.p. 213°–215° C.

| Analysis | % C | % H | % N |
|---|---|---|---|
| Calculated for $C_{13}H_9ClN_2O_4$: | 53.3 | 3.1 | 9.6 |
| Found: | 53.3 | 2.9 | 9.6 |

Step B

Sodium metal (11.5 g.) was dissolved in 250 ml of ethanol to provide sodium ethoxide. To this solution was added 3.0 g (0.010 mole) of 2-(2-chloroanilino)-3-nitrobenzoic acid and 0.76 g. of sodium borohydride. The mixture was heated at reflux for one day, cooled, and acidified with 10 percent hydrochloric acid. A solid product was collected by filtration, washed with water, and recrystallized from aqueous ethanol. The product was 9-ethoxyphenazine-1-carboxylic acid, in the form of an orange solid, m.p. 224°–226° C.

| Analysis | % C | % H | % N |
|---|---|---|---|
| Calculated for $C_{15}H_{12}N_2O_3$: | 67.1 | 4.5 | 10.4 |
| Found: | 66.8 | 4.3 | 10.8 |

This product was used as a starting material for the synthesis of the compound of Example 9.

Various modifications and alterations of this invention will be apparent to those skilled in the art without departing from the scope and spirit of this invention and the latter should not be restricted to that set forth herein for illustrative purposes.

What is claimed is:
1. Compounds of the formula:

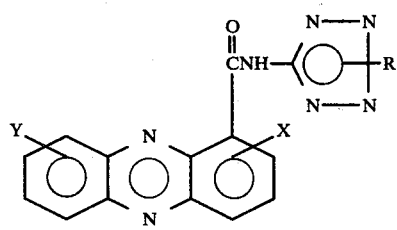

wherein R is a hydrogen atom or a $C_1$–$C_4$ alkyl group, X is a hydrogen atom, halogen atom, or a methoxy or methyl group, and Y is a hydrogen atom, halogen atom, or a methoxy or ethoxy group.

2. Compounds according to claim 1, wherein R is a hydrogen atom.

3. Compounds according to claim 1, wherein X is a hydrogen atom.

4. Compounds according to claim 1, wherein Y is a hydrogen atom.

5. Compounds according to claim 1, wherein Y is a methoxy or ethoxy group.

6. The compound N-(tetrazol-5-yl)phenazine-1-carboxamide according to claim 1.

7. The compound 9-ethoxy-N-(tetrazol-5-yl)-phenazine-1-carboxamide according to claim 1.

8. The compound 6-ethoxy-N-(tetrazol-5-yl)-phenazine-1-carboxamide according to claim 1.

9. The compound 8-ethoxy-N-(tetrazol-5-yl)-phenazine-1-carboxamide according to claim 1.

10. The compound 7-ethoxy-N-(tetrazol-5-yl)-phenazine-1-carboxamide according to claim 1.

11. Anti-allergic compositions, comprising at least one compound according to claim 1 together with a pharmaceutically acceptable carrier.

12. A method for combatting allergic reactions in a mammal which comprises administering to said mammal an effective dose, less than a toxic amount, of at least one composition according to claim 11.

13. A method according to claim 12, wherein said composition is administered orally.

* * * * *